(12) United States Patent
McHugh et al.

(10) Patent No.: US 7,205,115 B2
(45) Date of Patent: Apr. 17, 2007

(54) METHOD AND SYSTEM FOR STABILIZATION OF ARACHIDONIC ACID FOR USE IN PLATELET FUNCTION ASSAY

(75) Inventors: Sean McHugh, La Jolla, CA (US); Dennis Durbin, Solana Beach, CA (US)

(73) Assignee: Accumetrics, Inc., San Diego, CA (US)

( * ) Notice: Subject to any disclaimer, the term of this patent is extended or adjusted under 35 U.S.C. 154(b) by 0 days.

(21) Appl. No.: 11/119,360

(22) Filed: Apr. 28, 2005

(65) Prior Publication Data

US 2006/0246527 A1    Nov. 2, 2006

(51) Int. Cl.
   *G01N 33/53*    (2006.01)
(52) U.S. Cl. .................................................. 435/7.1
(58) Field of Classification Search .................. None
   See application file for complete search history.

(56) References Cited

U.S. PATENT DOCUMENTS

| 5,763,199 | A | | 6/1998 | Coller ..................... 435/7.21 |
| 5,922,551 | A | * | 7/1999 | Durbin et al. ............. 435/7.21 |
| 6,531,150 | B1 | * | 3/2003 | Sunohara et al. ........... 424/463 |
| 6,596,191 | B2 | * | 7/2003 | Sakamoto et al. ....... 252/188.28 |

OTHER PUBLICATIONS

Robert W. Colman, "Hemostasis and Thrombosis: Basic Principles and Clinical Practice", Section 30, pp. 472-485, 1st Edition, Lippincott Williams & Wilkins, 1982.
A. Bye, et al., "Effect of a Single Oral Dose of Aspirin on the Platelet Aggregation Response to Arachidonic Acid" British Journal of Clinical Pharmacology, 7, pp. 283-286, 1979.
S. Moncada, et al., "Arahidonic Acid Metabolites and the Interactions between Platelets and Blood-Vessel Walls", The New England Journal of Medicine, vol. 300, No. 20, pp. 1142-1147, 1979.
C.M. Ingerman, et al., "Hereditary Abnormality of Platelet Aggregation Attributable to Nucleotide Storage Pool Deficiency", Blood, vol. 52, No. 2, Aug. 1978.
David Stejskal, et al., "Application of Cationic Propyl Gallate as Inducer of Thrombocyte Aggregation for Evaluation Of Effectiveness of Antiaggregation Therapy", Biomedical Papers, vol. 145, No. 2, pp. 69-74, 2001.
Barry S. Coller, et al., "A Murine Monoclonal Antibody that Completely Blocks the Binding of Fibrinogen to Platelets Produces a Thrombasthenic-like State in Normal Platelets and Binds to Glycoproteins IIb and/or IIIa", The Journal of Clinical Investigation, vol. 72, pp. 325-338, Jul. 1983.
The Epic Investigators, "Use of a Monoclonal Antibody Directed Against the Platelet Clycoprotein IIb/IIIa Receptor in High-Risk Coronary Angioplasty" The New England Journal of Medicine, vol. 330, No. 4, pp. 956-961, Apr. 7, 1994.
Nigel S. Cook, et al., "Platelet Glycoprotein IIb/IIIa Antagonists", Drugs of the Future, 19(2):135-159, 1994.
Pedro Cuatrecasas, et al., "Protein Purification by Affinity Chromatography", The Journal of Biological Chemistry, vol. 245, No. 12, pp. 3059-3065, Jun. 25, 1970.

* cited by examiner

*Primary Examiner*—Christopher R. Tate
*Assistant Examiner*—Amanda P. Wood
(74) *Attorney, Agent, or Firm*—Heller Ehrman LLP; Paul Davis

(57) ABSTRACT

Methods and systems for rapidly determining the level of platelet inhibition in whole blood, due to aspirin usage, with a single use arachidonic based assay device that can be stored at room temperature is provided. A lyophilized assay reagent that contains arachidonic acid at sufficient concentration to maximally activate platelets is utilized. An antioxidant within the same lyophilized assay reagent reduces the oxidation rate of arachidonic acid but does not interfere with platelet function. An oxygen absorber within the single use assay device packaging creates an inert environment within a short period of time after package is sealed. The assay device can have a housing with a plurality of channels and a common blood sample introduction port coupled to each of a channel of the plurality of channels. The assay device can also include a lyophilized assay reagent that contains arachidonic acid at sufficient concentration to maximally activate platelets.

31 Claims, No Drawings

METHOD AND SYSTEM FOR STABILIZATION OF ARACHIDONIC ACID FOR USE IN PLATELET FUNCTION ASSAY

BACKGROUND OF THE INVENTION

1. Field of the Invention

The present invention is directed to methods and systems for stabilizing arachidonic acid (AA), and more particularly to methods and systems for stabilizing AA in a single use platelet function assay.

2. Description of the Related Art

The role of platelets in mammalian physiology is extraordinarily diverse, but their primary role is in promoting hemostasis. In many situations, an evaluation of the ability of blood to clot is desired, a parameter that is frequently controlled by the ability of platelets to adhere and/or aggregate. Of interest, therefore, is the assessment of the adhesive functions of platelets. For example, questions of interest include whether to administer drugs that will block, or promote, clot formation, or whether to detect deficiencies in platelet function prior to surgical procedures. Also of interest is evaluating the effectiveness of a platelet inhibitor that is being tested as a new drug or is being used as approved clinical treatment in a patient.

Platelet aggregation plays a key role in the pathogenesis of thrombosis and acute coronary artery disease. Evidence suggests that significant platelet function variability exists in the response to various anti-platelet agents. In particular, aspirin is widely used for its anti-platelet effects in patients with acute coronary syndromes (ACS). The clinical benefits of aspirin in ACS is due in part to its ability to inhibit thromboxane A2 (TXA2), known to cause platelet aggregation, by the irreversible acetylation of the cyclo-oxygenase 1 (COX-1) enzyme.

Platelet aggregation is a term used to describe the binding of platelets to one another. In vitro platelet aggregometry is the laboratory method used to assess the in vivo ability of platelets to form the aggregates leading to a primary hemostatic plug. In this technique an anti-coagulated whole blood sample is centrifuged under multiple conditions to create both a platelet-rich plasma (PRP) and platelet-poor plasma (PPP) sample. An aggregating agent is then added to the PRP and aggregation of platelets monitored optically while in parallel with this, a separate optical measurement is made using the PPP sample. The percent aggregation is then determined by use of the PPP channel as the 100% aggregation reference level to compare with the PRP channel.

Helena Laboratories (Beaumont, Tex.) a manufacturer of platelet aggregometry systems for laboratory use provides educational literature that suggests the appropriate aggregating agent depending upon the purpose of the test. For assessing the effects of aspirin on platelet function, Helena Laboratories states, "The arachidonic acid platelet aggregation assay is the only practical way to monitor the effects of aspirin therapy, now widely used to prevent strokes and heart attacks." Helena Laboratories, *Evaluation of Platelet Function Wall Chart* 586–25. Arachidonic acid is a fatty acid present in the granules and membranes of human platelets. Marcus A J: *Platelet lipids*. In Coleman R W, Hirsh J, Marder V J, Salzman E W: *Hemostasis and thrombosis: Basic principles and clinical practice*, pg 472. JB Lippencott Company, Philadelphia 1982. It is liberated from phospholipids and, in the presence of the enzyme cyclo-oxygenase one (COX-1), incorporates oxygen to form the endoperoxide prostaglandin G2 ($PGG_2$). $PGG_2$ is then quickly transformed to prostaglandin $H_2$ ($PGH_2$) which in turn is converted to thromboxane $A_2$ a potent inducer of platelet aggregation. Ingestion of aspirin or aspirin-containing compounds inhibits COX-1 mediated oxygen consumption, thus precluding all subsequent events leading to platelet aggregation. Bye A, Lewis Y, O'Grady J: *Effect of a single oral dose of aspirin on the platelet aggregation response to arachidonic acid*. Br J Clin Pharmac 7:283, 1979.

In vitro addition of arachidonic acid to normal platelet rich plasma results in a burst of oxygen consumption, thromboxane formation and platelet aggregation. Moncada S, Vane J R: *Arachidonic acid metabolites and the interactions between platelets and blood vessel walls*. N Eng J Med 300:1142, 1979. However, in the presence of aspirin or aspirin-containing compounds, these reactions are absent. Ingerman C M, Smith J B, Shipiro S, Sedar A, Silver A, Silver M J: *Hereditary abnormality of platelet aggregation attributable to nucleotide storage pool deficiency,* Blood 52:332, 1978.

The challenge with the use of arachidonic acid in clinical settings is the relatively unstable nature of the compound. When exposed to oxygen, arachidonic acid undergoes a process called autoxidation. Autoxidation is generally defined as a chemical reaction that usually takes place at ambient temperature between atmospheric oxygen and an organic compound. Common examples of the autoxidation phenomena are the browning of fruit, rusting of metal, and the degeneration of rubber products. Autoxidation causes arachidonic acid to turn yellow and deteriorate rapidly. In typical laboratory use, arachidonic acid is stored at −20° C. in sealed inert ampoules and once thawed, recommended to be used within 24 hours. Sigma-Aldrich Data Sheets A9673 and A8798. Alternatively, some manufacturers lyophilize a salt-based version of arachidonic acid but again the material must be stored in a sealed inert ampoule at −20° C. and used immediately upon opening. In the clinical setting there is often little advance notice of the need to run a particular test and the necessity to manage the amount of material to thaw and the subsequent use of the material in a timely manner is both cumbersome and time consuming.

Another aspect of the autoxidation of arachidonic acid, of particular relevance to its use as a platelet activator, is that the ex vivo autoxidation of arachidonic acid does not necessarily create the same by-products as in vivo oxidation and in some cases can produce stable by-products that mimic TXA2. Use of arachidonic acid that had degraded in this manner in an assay to assess the effects of aspirin would falsely indicate that aspirin was having no effect on platelet aggregation.

The autoxidation phenomena could be prevented by the total exclusion of oxygen or other oxidizing substances but this is generally not practical. Instead, what is more typically done is to utilize inhibitors that decrease the reaction rate or prolong the induction period. However complete prevention of autoxidation is unlikely. Substances that can suppress autoxidation are termed inhibitors or antioxidants. Preventive inhibitors decrease the rate of autoxidation by suppressing the rate of initiation reactions. Antioxidants in the true sense are substances that can inhibit propagation steps; that is, they interrupt autoxidation chain reactions because after giving up their electron they are still in a stable configuration. Antioxidants are commonly used in food preservation to keep foods from becoming rancid, browning, or developing black spots. Antioxidants also minimize the damage to some essential amino acids and the loss of some vitamins. The two common types of antioxidants used in foods are acids and phenolic compounds. Examples of acid antioxidants are ascorbic and citric acids, while phenolic antioxidant compounds include BHA, BHT, TBHQ, Tocopherols, Lecithin, THBP, Gum and Glycine.

Because of the difficulty with storage and handling, no clinical platelet function analyzer currently utilizes arachidonic acid to measure platelet response to aspirin. Instead, systems like the Dade Behring PFA-100® or Plateletworks® use a combination of platelet activators such as adenosine diphosphate (ADP), collagen and epinephrine. These systems however have shown poor sensitivity and specificity to the detection of aspirin impaired platelet function since their activation agonists are not specific to the pathway targeted by aspirin. The initial Accumetrics' VerifyNow™ Aspirin Assay used cationic propyl gallate (cPG) as the platelet agonist. cPG activates platelets by causing the release of platelet bound arachidonic acid from the phosopholipid layer and has been shown to provide a sensitive and specific activation of platelets along the pathway targeted by aspirin. Steiskal, et al, *Application of Cationic Propyl Gallate as Inducer of Thrombocyte Aggregation For Evaluation of Effectiveness of Antiaggregation Therapy.* The limitation of cPG however is that when used in whole blood versus PRP the activation of platelets is less consistent presumably due to the red blood cell's effect on the cationic charge.

A rapid platelet function assay has recently been developed and is described in U.S. Pat. No. 5,763,199. The assay determines glycoprotein (GP)IIb/IIIa receptor blockade in undiluted whole blood. Agglutination of small polymeric beads coated with a GPIIb/IIIa ligand such as fibrinogen results when the beads are contacted with whole blood containing platelets with activated GPIIb/IIIa receptors that are not blocked. Failure to agglutinate indicates either failure of the GPIIb/IIIa receptors to become activated and/or blockade of the GPIIb/IIIa receptors. In a preferred embodiment, the addition of a platelet activator like arachidonic acid, results in an assay that is rapid and convenient enough to be performed at the bedside and that results in agglutination of the small polymeric beads within a convenient, known period of time if the activation receptors are not blocked. The assay includes the ability to transfer blood to be tested from a collection container to an assay device without opening the collection container.

There is a need for a method for rapidly determining the level of platelet inhibition in whole blood, due to aspirin usage, with a single use arachidonic based assay device that can be stored at room temperature for many months.

SUMMARY OF INVENTION

Accordingly, an object of the present invention is to provide methods and systems for rapidly determining the level of platelet inhibition in whole blood, due to aspirin usage, with a single use arachidonic based assay device that can be stored at room temperature for many months.

These and other objects of the present invention are achieved in a method for producing single use assay devices for measuring platelet function. A lyophilized assay reagent, that contains arachidonic acid at sufficient concentration to maximally activate platelets; is utilized. An antioxidant within the same lyophilized assay reagent reduces the oxidation rate of arachidonic acid but does not interfer with platelet function. An oxygen absorber with sufficient capacity within the single use assay device packaging creates an inert environment within a short period of time after package is sealed.

In another embodiment of the present invention, an assay device for measuring platelet function has a housing with a plurality of channels and a common blood sample introduction port coupled to each of a channel of the plurality of channels. A plurality of reagents are included. Each of a reagent is positioned in a separate channel. The plurality of reagents includes, a lyophilized assay reagent that contains arachidonic acid at a sufficient concentration to maximally activate platelets, and an antioxidant within a same lyophilized assay reagent that reduces an oxidation rate of the arachidonic acid and not interfere with platelet function.

In another embodiment of the present invention, a assay device for measuring platelet function is provided and includes a lyophilized assay reagent that contains arachidonic acid at a sufficient concentration to maximally activate platelets. An antioxidant within a same lyophilized assay reagent reduces an oxidation rate of the arachidonic acid and does not interfere with platelet function. An oxygen absorber is provided with sufficient capacity within an assay device packaging. Packaging creates an inert environment within a short period of time of the assay device.

DETAILED DESCRIPTION OF THE PREFERRED EMBODIMENTS

In various embodiments of the present invention, a composition of arachidonic acid is utilized as an activator in measuring inhibition of platelet aggregation by cyclooxygenase-1 (COX-1). antagonists, including but not limited to aspirin, in whole blood samples. Accordingly, the aforementioned compositions may be employed to determine the effectiveness of anti-platelet therapy involving treatment of patients with aspirin. The above compositions may be employed in conjunction with particles coated with a GPIIb/IIIa receptor ligand and any other reagents necessary for conducting an assay for the efficacy of COX-1 inhibitors such as aspirin.

A lyophilized reagent composition may be used that comprises the aforementioned activator composition and particles. In one embodiment, a metered volume of a sample to be measured, such as whole blood, is mechanically mixed with the lyophilized reagent. A change in light transmission is monitored and an index of platelet activity calculated. In one embodiment, a whole blood sample is combined in a cuvette or a unitized cartridge with the aforementioned lyophilized reagent. An apparatus may be employed for carrying out the assay. The apparatus can include a well for receiving the sample where the well contains the lyophilized reagent and other reagents for conducting the assay. The additional reagents may be various buffers and/or lyophilization stabilizers, and the like.

In one embodiment, the sample has been affected by an arachidonic acid (AA) antagonist. For example, the sample may be from a patient undergoing treatment with aspirin. In one embodiment of the present invention, a combination is provided in an assay medium where the combination is the sample and a composition of AA with an anti-oxidant stabilizer, including but not limited to ascorbic acid, and the like. The final concentration of AA can be 0.5 to 10 mM, preferably, 0.75 to 2 mM and the final concentration of ascorbic acid can be 1 to 30 mM, and preferably 5 to 15 mM.

A reagent can be utilized that includes particles coated with a compound that can result in the specific agglutination of platelets, i.e., the agglutination of platelets by the specific interaction between a receptor on the platelets and the compound on the particles. Suitable compounds include, by way of illustration and not limitation, antibodies to a platelet receptor and GPIIb/IIIa receptor ligands, which may be a small organic molecule, polypeptide, protein, monoclonal antibody or nucleic acid that binds, complexes or interacts with GPIIb/IIIa receptors on the platelet surface. Platelet mediated aggregation of the particles results when the GPIIb/IIIa receptors on the surface of platelets bind, complex or otherwise interact with the GPIIb/IIIa receptor ligands on the particles. Suitable GPIIb/IIIa ligands include fibrinogen, monoclonal antibody 10E5 (Coller, et al., J. Clin. Invest. 72:325 (1983)), monoclonal antibody c7E3 (The EPIC Investigators, N.E. Journal of Med., 330:956 (1994)), von Willebrand factor, fibronectin, vitronectin and other ligands that have an arginine glycine-aspartic acid (RGD) sequence or other peptides or peptidomimetics that mimic this sequence (Cook, et al., *Drugs of the Future* 19:135 (1994)). Other compounds of interest include thrombin inhibitors, low molecular weight heparin, and so forth.

The particles to which the compound is attached are at least about 0.1 microns and not more than about 20 microns. In one embodiment, the particles are about 0.1 microns to about 10 microns. In another embodiment, the particles are at least about 1 micron and less than about 8 microns. The particles can be virtually any shape, but are generally spherical with uniform diameters. The particles may have any density, and in one embodiment a density approximating water, generally from about 0.7 to about 1.5 g/ml. The particles may or may not have a charge on the surface, either positive or negative, preferably negative. The particles are functionalized or functionalizable to covalently bind or attach such members at their surface, either directly or indirectly.

The particles may be solid (e.g., comprised of organic and inorganic polymers or latex), oil droplets (e.g., hydrocarbon, fluorocarbon, silicon fluid), or vesicles (e.g., synthetic such as phospholipids or natural such as cells and organelles). The solid particles are normally polymers, either addition or condensation polymers, which are readily dispersible in a liquid medium. Examples of suspendable particles include but are not limited to, polymeric materials such as latex, lipid bilayers, oil droplets, cells and hydrogels. Other particle compositions include but are not limited to, polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), polysaccharides such as dextrans and modified dextrans, etc.; either used by themselves or in conjunction with other materials. The solid particles can be polystyrene, polyacrylamide, homopolymers and copolymers of derivatives of acrylate and methacrylate, particularly esters and amides, silicones and the like.

The compound is coated on the particles, often by covalent attachment to the particles. Such covalent attachment can be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). Briefly, as mentioned above, the surface of the particle may be polyfunctional or be capable of being polyfunctionalized. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature (see above). The attachment of the side member may be directly by a bond or indirectly through the intermediacy of a linking group. The length of a linking group may vary widely, depending upon the nature of the side member and of the particle.

The ratio of molecules of compound to particle is controlled in the attachment of the molecules of compound to the particle. In one embodiment, the number of functionalized sites on the surface of the particle is controlled by adjusting the number of such sites introduced on the surface of the particle. Alternatively, or in conjunction with the preceding, the ratio of molecules of compound to particle may be controlled by adjusting the concentration of the compound in the reaction medium for the attachment.

The particle reagent employed in the present invention may be treated with a sufficient amount of material to block areas of adsorption on the particles. These materials do not affect the functioning of the particles. The blocking materials include but are not limited to, proteins such as bovine serum albumin, bovine gamma globulin, and the like, polysaccharides such as dextran, and the like. In another embodiment, which may be utilized in conjunction with the above, particles are employed wherein the number of functionalized sites for attachment substantially reduce the adsorption area on the surface of the particles.

The particles can comprise a label, either attached thereto or incorporated therein. The label may be any moiety that may be used for the purpose of detection. The label is often a member of a signal producing system. The label is capable of being detected directly or indirectly. The label can be isotopic or nonisotopic, usually non-isotopic, and can be a dye, fluorescent molecule, chemiluminescent molecule, a catalyst, such as an enzyme, a polynucleotide coding for a catalyst, promoter, coenzyme, enzyme substrate, radioactive group, a small organic molecule, amplifiable polynucleotide sequence, and the like.

In one specific embodiment of the present invention, the particles contain one or more dyes that absorb in the infrared. Such dyes include bacteriochlorin, bacteriochlorophytin, meropolymethine dyes, benzoannulenes, vinylogous porphorins, polymethine dyes, cyanines and merocyanines, and the like. Specific dyes include, Copper(II)-tetra-tert-butyl-tetrakis(dimethylamino)-29H-31H-phthalocyanine and Vanadyl-tetra-tert-butyl-tetrakis(dimethylamino)-29H-31H-phthalocyanine. The particular dye that is selected is one of convenience, availability, stability, compatibility with the particle and the like. These dyes may be incorporated directly into the particle itself, through polymerization or passive adsorption. The dyes may be loaded individually (i.e., sequentially) or in combination (i.e., simultaneously). Alternatively, the dyes may be linked to the bead in combination with the linking component, such that they do not leach from the surface. Irrespective of the loading method used, the conditions are such that the particle surface is unaffected with respect to the ability to agglutinate under appropriate conditions.

The dyes can absorb light in the range of about 750 nm–900 nm, particularly in the range of about 750–850 nm. For samples with high levels of red blood cells, the light is at about 800 nm±10 nm, which is the isobestic point for oxyhemoglobin and reduced hemoglobin. The amount of dye employed with the particles varies with the extinction coefficient of the dye in the light range of interest, the required sensitivity of the assay, the size of the particles, the mode of binding of the dye to the particles, compatibility of the dye with the particle matrix, and the like. The amount of dye incorporated can be in the range of about 1 to 20 weight percent, more usually 5 to 15 weight percent. Suitable dyes include but are not limited to, phthalocyanines, and the like. Metal free phthalocyanines absorb at approximately 700 nm (e=162,000). The metal complexes shift the absorption to either shorter or longer wavelength, most metals shift the absorption to a much shorter wavelength, but some, such as lead absorb at much longer wavelength than the metal free phthalocyanines.

The complexes formed between transition metals and phthalocyanines (metollophthalocyanines and Metallonaphthalocyanines) are chemically very stable to light and heat. They are formed by condensation of opthalodinitriles in the presence of an appropriate metal. Some of the metals used in the formation of the metalophthalocyanines besides the copper (Cu) and the Vanadium (V) are magnesium (Mg), zinc (Zn), and cobalt (Co).

In one specific embodiment of the invention carboxylated microparticles with a flat absorption maximum are employed. These microparticles are prepared by incorporating multiple dyes that have distinct absorption maximum close to 805 nm. This results in a flat maximum absorption spectrum across a broad range wavelength from 780–820 nm.

The sample may be any solution, synthetic or natural, to be analyzed where the sample has been subject to an effect from a COX-1 antagonist, particularly aspirin. The term sample includes biological tissue, including body fluids, from a host, and so forth. The sample can be examined directly or may be pretreated. The present invention has particular application to samples that comprise platelets, including body fluids such as, for example, whole blood, platelet-containing blood fractions such as plasma, and the like. In one embodiment the invention has particular application to whole blood samples. The amount of the sample depends on the nature of the sample. For fluid samples such as whole anticoagulated blood, the amount of the sample is usually about 30 µl to 5000 µl, preferably, about 100 to 300 µl. The term "sample" includes unprocessed samples directly from a patient or samples that have been pretreated and prepared in any convenient liquid medium, usually an aqueous medium (e.g., sodium citrate).

Preferably, the medium for conducting the assays in accordance with the present invention is an aqueous medium. Other polar cosolvents may also be employed in the medium, usually oxygenated organic solvents of from 1–6, more usually from 1–4 carbon atoms, including alcohols, ethers and the like. Usually, such cosolvents are present in less than about 70 weight percent, more usually, in less than about 30 weight percent. Additionally, various ancillary materials are frequently employed in the method in accordance with the present invention. For example, buffers are normally present in the assay medium, as well as stabilizers for the assay medium and the assay components; surfactants, particularly non-ionic surfactants; binding enhancers, e.g., polyalkylene glycols; or the like.

The pH for the medium can be in the range of about 2 to about 11, preferably, about 4 to about 9. Various buffers may be used to achieve the desired pH and maintain the pH during the method. Illustrative buffers include HEPES, borate, phosphate, carbonate, Tris, barbital, and the like. The particular buffer employed is not critical to the method but one buffer may be preferred over others in certain circumstances. In some circumstances HEPES is preferred and is present at a concentration of about 0.05M to about 0.001M but generally at a concentration of about 0.01M.

The volume of assay medium can be about 25 to about 500 microliters, usually about 75 to about 250 microliters. The assays may be carried out in any suitable container. Conveniently, the container is a cuvette or cartridge that is used with the instrument for carrying out the assay and measuring the assay results. The reaction container usually contains the activation initiator in accordance with the present invention in dry lyophilized form together with other reagents such as the particle reagent and the like, stabilizers and so forth.

The combination of sample and particle reagent is incubated under conditions for agglutinating the particles. Moderate temperatures are normally employed for carrying out the method. The temperature may be constant or may vary. Usually, a constant temperature is employed during the reaction step. The temperature employed can be about 10 to about 80° C., more usually, about 15 to about 45° C., preferably, the temperature is at least 25° C., more preferably in the range of about 30 to about 40° C., usually about 37° C.

The extent of agglutination of the particles is determined and is related to the presence and/or amount of the member in the sample. The presence of agglutination may be determined visually by observing clumping of the particles, which would indicate agglutination. Preferably, as mentioned above, the particles may be colored to aid in visualizing agglutination or clumping of the matrix. The extent of agglutination may be measured spectrophotometrically, turbidimetrically, nephelometrically, and the like, by observing the rate of change of optical density of the medium, and the like.

In a specific embodiment of the present invention, an assay for platelet function activity is conducted on a whole blood sample from a patient undergoing treatment with aspirin. The sample is combined in a suitable container, e.g., reaction cuvette, with fibrinogen coated particles, and the composition of AA and ascorbic acid to form an assay medium. The particles of the particle reagent have one or more infrared dyes incorporated therein. The combination is subjected to agglutination conditions. Then, the medium is irradiated with light in the infrared region. The transmission of infrared light from the assay mixture is determined where the level of transmission is related to platelet function activity.

The agglutination medium is selected to have high absorption at ~800 nm. The ratio between the agglutination medium absorption coefficient and whole blood absorption coefficient should preferably be greater than about 4:1 at 800 nm. The absorption ratio for a particular assay is a function of both the absorption coefficient of the agglutination medium and the concentration of the agglutination medium in the assay sample.

After the sample has been combined with the reagents, it can be heated to a temperature above room temperature, but below that which would interfere with the assay, so as to insure that the temperature can be controlled without adversely affecting the assay result. Desirably, the temperature can be at least 25°, preferably in the range of 30–40° C., more preferably about 37° C. The reaction medium is usually gently agitated upon combining of the reagents with the sample and during the period of the reaction. Agitation is sufficient to achieve and maintain homogeneity in the assay samples. The total time of the readings from the zero time (time of mixing), may range from about 10 sec. to 10 min., more usually about 30 sec. to 8 min., and preferably about 30 sec. to 3 min. The data may be analyzed by any convenient means, particularly using an algorithm that can manipulate the data in relation to calibrators and/or controls.

The level of agglutination is an indication of the platelet function activity of the sample tested. The level of agglutination may be compared against a standard of known platelet function activity. Usually, the result will be compared to a calibrator, which may be performed concomitantly or have been performed previously or may be provided as a standard curve.

The method of the present invention may be employed in conjunction with an assay for platelet count such as that described in U.S. patent application Ser. No. 09/177,884 filed Oct. 23, 1998 (the '884 application), the relevant disclosures of which are incorporated herein by reference.

The above assays preferably may be conducted in a device, which allows the reactions in accordance with the present invention to occur and which measures the results thereof. The instrument can assess platelet function based upon the ability of activated platelets to bind fibrinogen. As activated platelets bind and agglutinate fibrinogen-coated particles, there is an increase in light transmittance. In general, an instrument to measure the result of the assay is one that can measure agglutination. Preferably, the instrument measures a change in optical signal due to agglutination. Suitable instruments include, by way of illustration and not limitation a kinetic spectrophotometer, Ultegra System® instrument (commercially available from Accumetrics, San Diego, Calif.) and employed for rapid platelet function activity measurements on normal samples), and the like.

The Ultegra® System instrument is a turbidometric based optical detection system, that measures platelet induced aggregation as an increase in light transmittance. The system consists of an analyzer, disposable cartridge and controls. The cartridge contains reagents based on microparticle agglutination technology. The quality control system includes an electronic control, two levels of assayed "wet" controls (WQC), an in-cartridge humidity sensor, an in-packaging temperature indicator, and a test for concurrence of two assay channels. The analyzer controls assay sequencing, establishes the assay temperature, controls the reagent-sample mixing for the required duration, determines the degree of platelet function, displays the result and performs self-diagnostics. For use in the present methods the test cartridge of the system contains a lyophilized preparation comprising particles with covalently attached GPIIb/IIIa receptor ligand, a composition of and ascorbic acid, and buffer. The patient sample is usually citrated whole blood, which is automatically dispensed from the blood collection tube into the cartridge by the analyzer, with no blood handling required by the user. The interaction is monitored by the infrared absorbency characteristics of the particles. As the particles interact with the platelets, the agglutination of the particles is measured through the optical system of the Ultegra™ analyzer. The agglutination is detected as an increase in the transmission of infrared light through the sample. The reaction kinetics are analyzed and translated into "Aspirin Response Units", ARU.

In another embodiment of the present invention, a kit is provided that includes in packaged combination a lyophilized preparation comprising particles with covalently attached fibrinogen, composition of M and ascorbic acid, and buffer. The lyophilized preparation may be present in a reaction container such as a cartridge used in the instrument of analysis. For the Ultegra® System, the lyophilized preparation may be placed in the outer wells of the four-well cartridge used in the analyzer. The kit may also include a sample collection container and/or a device for carrying out the present method. The relative amounts of reagents may be varied widely to provide for concentrations in solution of the reagents that substantially optimize the sensitivity of a determination.

Where appropriate, the reagents can be placed in an air-tight package in order to maintain the activity of any reagents. The package may be, for example, a bag, pouch, or the like fabricated from a material that is substantially non-permeable to moisture. Such materials include, by way of example and not limitation, plastic, aluminum foil, and the like. Furthermore, the package may contain a desiccant pouch and an oxygen absorber to maintain a dry oxygen free environment. The oxygen absorber may be like the Pharmakeep KC-20 from MGC or similar. The oxygen absorber should have an absorption capacity in the range of 1 to 50 mL and ideally from 20 to 30 mL. For blood samples the kit may also include an article for piercing a person's skin, disinfectant or sterilizing pads and so forth. The kit may also include calibrators and standards.

The kit can include the reagents necessary for carrying out the assay of the present invention. In one embodiment, the kit includes a blood vial, a buffer that maintains the pH and salt concentration of the blood sample assessed within ranges suitable for platelet mediated agglutination of the solid surface and small polymeric beads coated with platelet GPIIb/IIIa receptor ligand. The buffer can be in solution, or can consist solely of the buffering composition and salts to which a known amount of water is added to give the desired buffer solution. Optionally, the kit can also comprise an anticoagulant. In one embodiment, the buffer is HEPES; the anticoagulant is citrate; a GPIIb/IIIa receptor ligand is fibrinogen; small polymeric beads are polyacrylonitrile or carboxylated polystyrene in which a peptide GPIIb/IIIa receptor ligand, such as fibrinogen, is covalently bonded to the bead surface by means of a covalent bond between the N-terminus of the peptide and an N-hydroxysuccinimide or carboxylate group on the bead surface in a further embodiment, the kit additionally comprises a platelet activator, such as a AA.

In one embodiment of the present invention, a single use assay reagent containing AA is provided that can be stored at room temperature for three months or more.

EXAMPLE 1

In a specific embodiment of the present invention, an assay for platelet function activity is conducted on a whole blood sample from a patient undergoing treatment with aspirin. The sample is combined in a suitable container, e.g., reaction cuvette, with a reagent that includes particles coated with a compound that results in a specific agglutination of platelets, to form an assay medium. The compound is an antibody to a platelet receptor and GPIIb/IIIa receptor ligands. The particles have one or more infrared dyes incorporated therein. The combination is subjected to agglutination conditions. The medium is irradiated with light in the infrared region using the Ultegra® System. The transmission of infrared light from the assay mixture is determined where the level of transmission is related to platelet function activity.

EXAMPLE 2

In a specific embodiment of the present invention, an assay for platelet function activity is conducted on a whole blood sample from a patient undergoing treatment with aspirin. The sample is combined in a suitable container, e.g., reaction cuvette, with a reagent that includes particles coated with a compound that results in a specific agglutination of platelets, to form an assay medium. The compound is an antibody to a platelet receptor and GPIIb/IIIa receptor ligands that is selected from, fibrinogen, monoclonal antibody 10E5, monoclonal antibody c7E3, von Willebrand factor, fibronectin, vitronectin, ligands that have an arginine glycine-aspartic acid (RGD) sequence, and other peptides or peptidomimetics that mimic this sequence. The particles have one or more infrared dyes incorporated therein. The combination is subjected to agglutination conditions. The medium is irradiated with light in the infrared region using the Ultegra® System. The transmission of infrared light from the assay mixture is determined where the level of transmission is related to platelet function activity.

EXAMPLE 3

In a specific embodiment of the present invention, an assay for platelet function activity is conducted on a whole blood sample from a patient undergoing treatment with aspirin. The amount of sample analyzed is about 30 µl to 5000 µl to 300 µl. The sample is combined in a suitable container, e.g., reaction cuvette, with a reagent that includes particles coated with a compound that results in a specific agglutination of platelets, to form an assay medium. The compound is an antibody to a platelet receptor and GPIIb/IIIa receptor ligands. The particles have one or more infrared dyes incorporated therein. The combination is subjected to agglutination conditions. The medium is irradiated with light in the infrared region using the Ultegra® System. The transmission of infrared light from the assay mixture is determined where the level of transmission is related to platelet function activity.

EXAMPLE 4

In a specific embodiment of the present invention, an assay for platelet function activity is conducted on a whole blood sample from a patient undergoing treatment with aspirin. The sample is combined in a suitable container, e.g., reaction cuvette, with a reagent that includes particles coated with a compound that results in a specific agglutination of platelets, to form an assay medium. The compound is an antibody to a platelet receptor and GPIIb/IIIa receptor ligands. The particles have one or more infrared dyes incorporated therein. A buffer is provided and the pH is is about 2 to about 11. The combination is subjected to agglutination conditions. The medium is irradiated with light in the infrared region using the Ultegra® System. The transmission of infrared light from the assay mixture is determined where the level of transmission is related to platelet function activity.

EXAMPLE 5

In a specific embodiment of the present invention, an assay for platelet function activity is conducted on a whole blood sample from a patient undergoing treatment with aspirin. The sample is combined in a suitable container, e.g., reaction cuvette, with utilizing a reagent that includes particles coated with a compound that results in a specific agglutination of platelets, to form an assay medium. The compound is an antibody to a platelet receptor and GPIIb/IIIa receptor ligands. The particles of the particle reagent have one or more infrared dyes incorporated therein. The volume of the assay medium is about 25 to about 500 microliters. The combination is subjected to agglutination conditions. The medium is irradiated with light in the infrared region using the Ultegra® System. The transmission of infrared light from the assay mixture is determined where the level of transmission is related to platelet function activity.

EXAMPLE 6

In a specific embodiment of the present invention, an assay for platelet function activity is conducted on a whole blood sample from a patient undergoing treatment with aspirin. The sample is combined in a suitable container, e.g., reaction cuvette, with utilizing a reagent that includes particles coated with a compound that results in a specific agglutination of platelets, to form an assay medium. The compound is an antibody to a platelet receptor and GPIIb/IIIa receptor ligands. The particles of the particle reagent have one or more infrared dyes incorporated therein. The combination is subjected to agglutination conditions and incubated at a temperature of at least 25°. The medium is irradiated with light in the infrared region using the Ultegra® System. The transmission of infrared light from the assay mixture is determined where the level of transmission is related to platelet function activity.

EXAMPLE 7

In a specific embodiment of the present invention, an assay for platelet function activity is conducted on a whole blood sample from a patient undergoing treatment with aspirin. The sample is combined in a suitable container, e.g., reaction cuvette, with utilizing a reagent that includes particles coated with a compound that results in a specific agglutination of platelets, to form an assay medium. The compound is an antibody to a platelet receptor and GPIIb/IIIa receptor ligands. The particles of the particle reagent have one or more infrared dyes incorporated therein. The combination is subjected to agglutination conditions and incubated at a temperature of at least 25°. The medium is irradiated with light in the infrared region using the Ultegra® System. The transmission of infrared light from the assay mixture is determined where the level of transmission is related to platelet function activity. Agglutination of the particles is detected as an increase in transmission of infrared light through the sample.

The foregoing description of embodiments of the invention have been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method for determining platelet inhibition in a whole blood sample from a person treated with the anti-platelet agent, aspirin, comprising:
    providing within a single use assay device packaging a lyophilized assay reagent that contains arachidonic acid at a sufficient concentration to activate platelets from the whole blood sample and an antioxidant that reduces the oxidation rate of the arachidonic acid and does not interfere with activation,
    wherein said single use assay device packaging further comprises an oxygen absorber to create an inert environment following packaging of said single use assay device, and
    wherein said single use assay device can be stored at room temperature for at least three months; and
    combining said whole blood sample with said assay reagent within a suitable container and measuring the agglutination of platelets in said sample.

2. The method of claim 1, wherein the lyophilized assay reagent is particles coated with a GPIIb/IIIa receptor ligand.

3. The method of claim 1, wherein the lyophilized assay reagent includes particles coated with a compound that results in a specific agglutination of platelets.

4. The method of claim 3, wherein the compound is selected from an antibody to a platelet receptor and GPIIb/IIIa receptor ligands.

5. The method of claim 4, wherein the GPIIb/IIIa receptor ligand is selected from fibrinogen, monoclonal antibody 10E5, monoclonal antibody c7E3, von Willebrand factor, fibronectin, vitronectin, ligands that have an arginine glycine-aspartic acid (RGD) sequence, and other peptides or peptidomimetics that mimic this sequence.

6. The method of claim 3, wherein the particles are sized from about 0.1 microns and about 20 microns.

7. The method of claim 3, wherein the particles are sized from about 0.1 microns to about 10 microns.

8. The method of claim 3, wherein the particles are sized from about 1 micron to no more than 8 microns.

9. The method of claim 3, wherein the particles have a density of about 0.7 to about 1.5 g/ml.

10. The method of claim 3, wherein the particles are functionalized or functionalizable to covalently bind.

11. The method of claim 3, wherein the compound is coated on the particles.

12. The method of claim 11, wherein the compound is coated on the particles by covalent attachment.

13. The method of claim 3, wherein a ratio of molecules of compound to particles is controlled in the attachment of molecules of compound to the particle.

14. The method of claim 3, wherein the particles have blocked areas of adsorption.

15. The method of claim 3, wherein the particles include a label.

16. The method of claim 15, wherein the label is a moiety used for the purpose of detection.

17. The method of claim 3, wherein the particles include at least one dye that absorbs in the infrared.

18. The method of claim 1, wherein an amount of sample analyzed is about 30 µl to 5000 µl.

19. The method of claim 3, wherein the sample is treated with an aqueous medium.

20. The method of claim 19, wherein a polar co-solvent is used with the aqueous medium.

21. The method of claim 19, wherein the aqueous medium includes at least one buffer.

22. The method of claim 21, wherein a pH of the aqueous medium is about 2 to about 11.

23. The method of claim 21, wherein a pH of the aqueous medium is about 4 to about 9.

24. The method of claim 19, wherein a volume of the aqueous medium is about 25 to about 500 microliters.

25. The method of claim 19, wherein a volume of the aqueous medium is about 75 to about 250 microliters.

26. The method of claim 19, further comprising:
    incubating the sample and the aqueous medium to agglutinate the particles.

27. The method of claim 26, further comprising:
    measuring the agglutination of the particles to determine platelet function activity.

28. The method of claim 26, wherein the sample and the aqueous medium are incubated at a temperature of at least 25°.

29. The method of claim 26, wherein the sample and the aqueous medium are incubated at a temperature of about 30–40° C.

30. The method of claim 27, further comprising:
    comparing a measured agglutination of the particles against a standard of known platelet function activity.

31. The method of claim 27, wherein agglutination of the particles is detected as an increase in transmission of infrared light through the sample.

* * * * *